United States Patent [19]

Ryan et al.

[11] Patent Number: 5,108,416
[45] Date of Patent: Apr. 28, 1992

[54] STENT INTRODUCER SYSTEM

[75] Inventors: Carol A. Ryan; Kim T. Chiev, both of Lowell, Mass.

[73] Assignee: C. R. Bard, Inc., Murray Hill, N.J.

[21] Appl. No.: 480,148

[22] Filed: Feb. 13, 1990

[51] Int. Cl.⁵ ............................................. A61M 29/00
[52] U.S. Cl. ........................................ 606/194; 623/1; 604/96
[58] Field of Search ............... 606/191, 194, 195, 192; 604/96, 104; 623/1, 12

[56] References Cited

U.S. PATENT DOCUMENTS

| | | |
|---|---|---|
| 3,502,069 | 3/1970 | Silverman . |
| 4,140,126 | 2/1979 | Choudhury . |
| 4,503,569 | 3/1985 | Dotter . |
| 4,512,762 | 4/1985 | Spears . |
| 4,553,545 | 11/1985 | Maass et al. . |
| 4,560,374 | 12/1985 | Hammerslag . |
| 4,580,568 | 4/1986 | Gianturco . |
| 4,641,563 | 2/1987 | Rockey . |
| 4,649,922 | 3/1987 | Wiktor ................................ 606/194 |
| 4,655,771 | 4/1987 | Wallsten . |
| 4,660,560 | 4/1987 | Klein . |
| 4,665,918 | 5/1987 | Garza et al. . |
| 4,681,110 | 7/1987 | Wiktor ................................ 606/194 |
| 4,732,152 | 3/1988 | Wallsten et al. . |
| 4,733,665 | 3/1988 | Palmaz ................................ 623/1 |
| 4,739,762 | 4/1988 | Palmaz . |
| 4,740,207 | 4/1988 | Kreamer ................................ 623/1 |
| 4,762,128 | 8/1988 | Rosenbluth . |
| 4,768,507 | 9/1988 | Fischell et al. . |
| 4,776,337 | 10/1988 | Palmaz . |
| 4,793,348 | 12/1988 | Palmaz . |
| 4,795,458 | 1/1989 | Regan . |
| 4,800,882 | 1/1989 | Gianturco ............................. 606/194 |
| 4,878,906 | 11/1989 | Lindemann et al. . |
| 4,878,908 | 11/1989 | Martin et al. ......................... 623/1 |
| 4,886,062 | 12/1989 | Wiktor . |
| 4,893,623 | 1/1990 | Rosenbluth ........................... 606/192 |
| 4,907,336 | 3/1990 | Gianturco . |
| 4,922,905 | 5/1990 | Strecker . |
| 4,950,227 | 8/1990 | Savin et al. ............................ 623/1 |
| 4,954,126 | 9/1990 | Wallstein ............................... 623/1 |
| 4,969,458 | 11/1990 | Wiktor . |

OTHER PUBLICATIONS

Palmaz et al., "Expandable Intraluminal Graft: A Preliminary Study", Radiology, 156: 73-77 (1985).
Palmaz et al., "Expandable Intraluminal Vascular Graft: A Feasibility Study", Surgery, 99: 199-204, (1986).
Palmaz et al., "Atherosclerotic Rabbit Aortas:Expandable Intraluminal Grafting", Radiology, 160: 723-726, (1986).
Wright et al., "Percutaneous Endovascular Stents: An Experimental Evaluation", Radiology, 156: 69-72, (1985).
Wallace et al., "Trachobronchial Tree: Expandable Metallic Stents Used in Experimental and Clinical Applications", Radiology, 158: 309-312, (1986).
Charnsangavej et al., "Stenosis of the Vena Cava: Preliminary Assessment with Expandable Metallic Stents", Radiology, 161: 295-298, (1986).
Rosch et al., "Experimental Intrahepatic Portacaval Anastomosis: Use of Expandable Gianturco Stents", Radiology, 162: 481-485, (1987).

(List continued on next page.)

Primary Examiner—John D. Yasko
Assistant Examiner—William W. Lewis
Attorney, Agent, or Firm—Wolf, Greenfield & Sacks

[57] ABSTRACT

A system for introducing a stent into a patient at a site of stenosis is disclosed. The system comprises a balloon catheter having a stent surrounding the balloon portion of the catheter. At least one stent-retaining means is located adjacent to at least one end of the balloon to retain the stent in position on the catheter until the balloon is inflated. Upon inflation of the balloon, the stent is expanded and the retention means releases the stent. The balloon is then deflated and the catheter is removed from the patient, leaving the expanded stent in place.

43 Claims, 16 Drawing Sheets

OTHER PUBLICATIONS

Sigwart et al., "Intravascular Stents to Prevent Occlusion and Restenosis After Transluminal Angioplasty", NEJM, 316: 701–706, (1987).

Schatz et al., "Balloon-Expandable Intracoronary Stents in the Adult Dog", Circulation 76: 450–457, (1987).

Roubin et al., "Early and Late Results of Intracoronary Arterial Stenting After Coronary Angioplasty in Dogs", Circulation, 76: 891–897, (1987).

Zollikofer et al., "Endovascular Stenting of Veins and Grafts: Preliminary Clinical Experience", Radiology, 167: 707–712, (1988).

Barth et al., "Flexible Tantalum Stents Implanted in Aortas and Iliac Arteries: Effects in Normal Canines", Radiology, 175: 91–96 (1990).

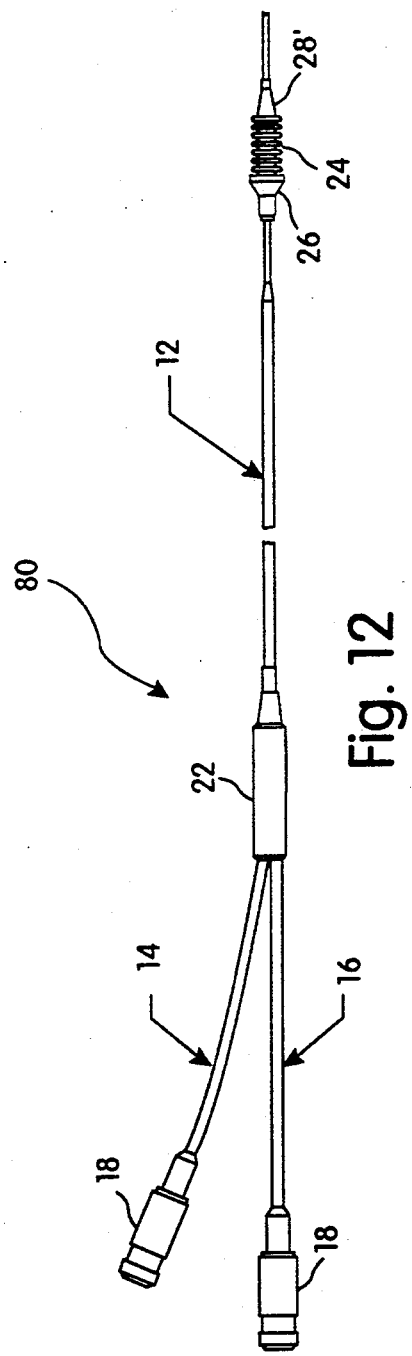

STENT INTRODUCER SYSTEM

FIELD OF THE INVENTION

This invention relates to percutaneous transluminal angioplasty, to stents for maintaining a treated stenosis in an open configuration and to a delivery system for placing the stent in a patient's artery.

BACKGROUND OF THE INVENTION

In recent years percutaneous transluminal angioplasty has become a common procedure for use in treating an obstruction (stenosis) in an artery. The treatment results in improved blood flow and circulation through the treated artery.

Although the most common type of treatment involves the use of a balloon catheter that is advanced through the patient's arteries into the stenosis and is then expanded under pressure to dilate the stenosis, other techniques for enlarging the stenosed region of the artery are under development.

The term "angioplasty" as used in this specification is intended to mean not only the treatment of stenoses with a balloon catheter but is intended to encompass other modes for treating stenoses such as with laser catheters, atherectomy catheters or the like. When angioplasty is performed on the coronary arteries, the procedure is referred to generally as percutaneous transluminal coronary angioplasty (PTCA). PTCA is an alternative to coronary bypass surgery. The PTCA procedure is of relatively short duration and involves puncturing the skin and an artery (usually the femoral artery in the patient's leg) to provide access to the patient's arterial system for the PTCA catheter. The PTCA catheter is navigated through the patient's arteries until it reaches the coronary artery to be treated. Typically, a patient undergoing PTCA will have a hospital stay of one or two days and will be able to resume full activity shortly thereafter. In contrast, treatment of a stenosed artery by coronary bypass surgery involves a very extensive and expensive operation with a long recuperative period.

In a significant number of angioplasty cases, the region of the artery where the angioplasty was performed may reclose, either as a result of acute closure or as a result of restenosis. Acute closures are vascular emergencies in which the artery collapses during or immediately after the angioplasty procedure. Such events are usually caused by damage to the artery or by a thrombus. Restenosis, on the other hand, occurs at a much later date, usually some weeks or months after the procedure. The restenosis may result from redevelopment of stenotic material (e.g., fatty material, cholesterol deposits, etc.) in the artery or from trauma to the interior surfaces of the artery which occurs during catheter placement or withdrawal. Follow up data for PTCA procedures has indicated that a small percentage of patients develop acute closure within one hour after the PTCA treatment and approximately 30% redevelop a restenosis within six months after the PTCA treatment. This restenosis will require further treatment either by one or more subsequent angioplasty treatments or, possibly, and ultimately by coronary artery bypass surgery.

A number of techniques and devices have been proposed to solve the problem of restenosis. Among them has been to insert a generally tubular element, referred to as a stent, in the artery at the site of the stenosis after the angioplasty is performed. The tubular element is introduced in a low profile condition (e.g., a small effective cross-sectional diameter), is placed in the artery at the region of the angioplasty and is then expanded into engagement with the wall of the artery. For example, U.S. Pat. No. 4,740,207 to Kreamer discloses a generally tubular stent having a spiral cross-section. The stent is delivered to the site of the angioplasty by mounting it on the balloon of a balloon catheter and then advancing the balloon catheter, carrying the stent, into the artery. When the balloon and stent are positioned at the site of the angioplasty, the balloon is inflated to expand the stent into engagement with the artery wall. The stent disclosed in the Kreamer patent incorporates a latching mechanism by which the stent locks in the expanded configuration so that it will be securely retained within the artery. The balloon catheter then may be deflated and removed from the patient. In placing the stent, it is important that the delivery catheter have a low profile, that it hold the stent securely in its collapsed configuration, that it enable easy expansion and release of the stent and that it permits the delivery catheter to be withdrawn. It is among the general objects of the invention to provide such a delivery catheter.

SUMMARY OF THE INVENTION

In accordance with the invention, the delivery catheter includes an elongate flexible shaft having a balloon mounted at its distal end. The balloon can be fabricated from a variety of polymeric materials such as polyethylene terephthalate (PET), polyolefin, nylon, or vinyl with polyolefins being preferred. The stent is mountable, in a contracted configuration on the balloon. The balloon may be expanded under low pressure sufficiently to engage the interior of the stent. The balloon is inflatable to a diameter to cause the stent to expand into firm engagement with the artery wall. In order to secure the stent on the catheter during delivery and to facilitate release of the stent, the delivery catheter is provided with at least one outer end cap located at the proximal end of the balloon. Another end cap may be located at the distal end of the balloon. The end caps engage and secure the mounted stent to prevent it from inadvertently slipping off of the balloon. The outer end cap is resilient and yieldable. When the balloon is inflated to expand and place the stent, the end cap resiliently yields and automatically releases the stent in response to the balloon expansion. After the stent has been placed, the balloon is collapsed and the end cap will return, under the influence of its own resilience, to the contracted configuration. When contracted, the balloon and the end cap have a profile smaller than the interior diameter of the expanded stent so that the delivery catheter can be withdrawn through the stent.

It is among the general objects of the invention to provide an improved stent delivery system for use as an adjunct to angioplasty.

Another object of the invention is to provide an improved stent delivery system that is of simple construction.

A further object of the invention is to provide an improved stent delivery system that is easy to use and operate.

Another object of the invention is to provide a stent delivery system that includes a catheter having at least one resilient retaining element adapted to engage the stent when the stent is mounted on a catheter and to release the stent when the stent is expanded.

A further object of the invention is to provide an improved stent delivery system having at least one retainer as described above in which the retainer is self-collapsing to facilitate withdrawal of the delivery system

DESCRIPTION OF THE DRAWINGS

The foregoing and other objects and advantages of the invention will be appreciated more fully from the following further description thereof, with reference to the accompanying drawings wherein:

FIG. 12 is an illustration of a second embodiment of the stent delivery system employing a modified end cap at the distal end of the introducer;

DETAILED DESCRIPTION OF THE INVENTION

The stent delivery system of the present system can be used to place a stent at a site of stenosis either subsequently, or as an alternative, simultaneously with a dilatation procedure employing a balloon dilatation catheter. In the former case, a balloon dilatation catheter is navigated to the stenosis site and positioned to place the balloon within the stenosis. The balloon then is inflated to press against the stenosis, thereby causing the lumen through the stenosis to be enlarged. The dilatation catheter then is withdrawn and exchanged for the stent delivery catheter. The delivery catheter is navigated to the site of the dilatation to place the stent in the dilated stenosis and the stent then is expanded. The delivery catheter then is withdrawn, leaving the expanded stent in place at the treatment site. Alternatively, in the latter case, a separate balloon dilatation catheter is not used. Rather, the stent delivery catheter is navigated to the stenosed site to position the unexpanded stent across the stenosis. The stent is then expanded, thereby simultaneously dilating the stenosis and expanding the stent. The delivery catheter then is withdrawn, leaving the expanded stent in place.

The stent introducer of the present invention can be used with a variety of expandable stents, both those known in the art and those yet to be developed. Accordingly, stents formed of rolled rectangular polymer sheets such as those described in the previously incorporated U.S. Pat. No. 4,740,207 to Kreamer, as well as stents formed of curved sections of metal wire such as those described in U.S. Pat. No. 4,800,882 to Gianturco (incorporated herein by reference) are intended to be contemplated for use in conjunction with the present invention.

Figure 1A:
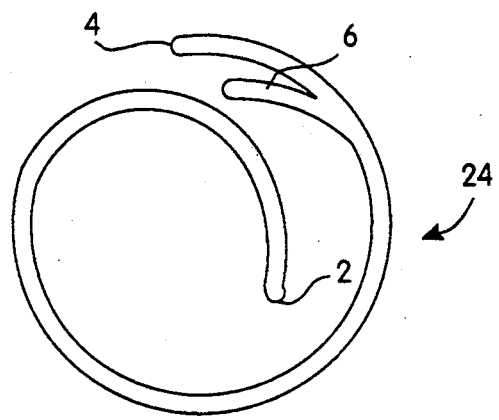
FIGS 1A and 1B are illustrations of one embodiment of a stent.
Figure 1B:
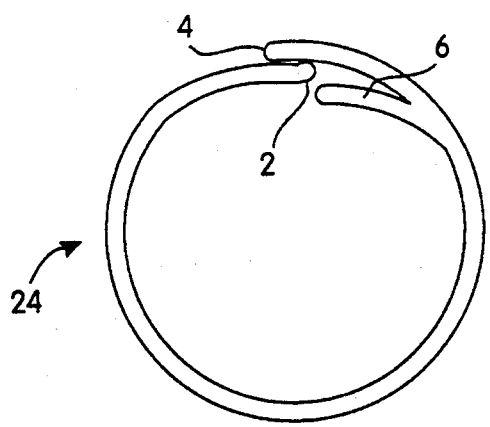

The stent described by Kreamer in U.S. Pat. No. 4,740,207 is shown in FIGS. 1A and 1B. The stent 24, generally comprises a semi-rigid, resilient tube made of a material suitable for long-term residence within a blood vessel. In its relaxed, unexpanded state, the tube is generally cylindrical having a relatively small diameter and a cross section which is a section of a spiral. One edge of the tube 4, preferably the outer portion of the spiral, has a retaining ledge 6. Upon expansion of that stent, the cylindrical tube becomes partially unrolled. This results in a cylinder having a larger diameter. If the cylinder is expanded sufficiently, the formerly inner region of the spiral 2 will be engaged by the retaining ledge 6, thereby locking the cylinder in its expanded configuration.

Figure 2:
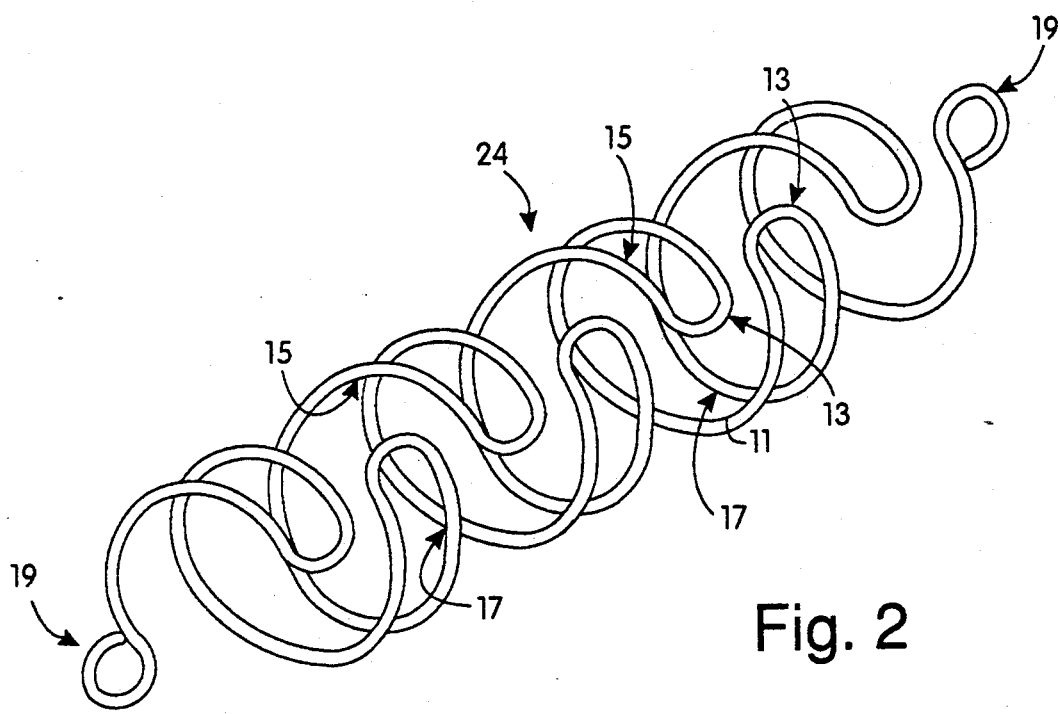
FIG. 2 is an illustration of a second embodiment of a stent.

The stent described by Gianturco in U.S. Pat. No. 4,800,882 is shown in FIG. 2. The stent 24 generally comprises a length of wire having a plurality of curved sections 11 that are formed into a generally circular configuration. Adjacent curved sections are joined by a bend or cusp 13, so that a series of alternating opposing loops 15, 17 are formed. A loop 19 is formed at each free end of the wire stent in order to shield the wire end. The resulting stent has a cylindrical shape with a longitudinal opening through which a deflated balloon catheter can be inserted. The opposing loops are tightly contracted around the balloon so that the cylindrical shape has an overlapping region in which portions of adjacent loops longitudinally overlap. When the balloon is inflated, adjacent loops diverge circumferentially relative to each other, thereby decreasing the overlapping region while increasing the diameter of the cylindrical shape. The expanded diameter of the stent is retained by a plastic deformation of the wire that occurs during the expansion. Once the expanded configuration has been achieved, the balloon catheter is withdrawn.

In one embodiment, a bioresorbable polymeric material can be used to form a stent which is otherwise similar in construction to that shown in the previously described Kreamer patent. Such an embodiment is desirable because it will help to maintain patency of the blood vessel for an extended period of time while still being less than a permanent fixture within the patient.

In a broad sense, the stent delivery system of the present invention comprises an apparatus for inserting a stent into a patient and expanding the stent at a site of stenosis, wherein the apparatus includes a means for releaseably retaining the stent. More specifically, the apparatus comprises a modified dilatation catheter having an expandable balloon at its distal end and at least one flexible end cap which serves to retain the stent on the balloon until the stent is expanded at a desired location within the patient.

Figure 3:
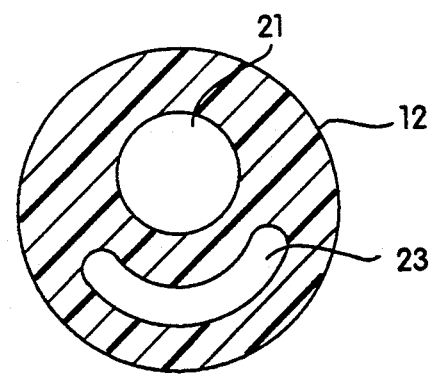
FIG. 3 is a cross-sectional view of one embodiment of a catheter shaft useful in the stent delivery system.

In one embodiment, shown in FIG. 3, the catheter shaft 12 has a guidewire lumen 21, and a balloon inflation lumen 23. The shaft is constructed of a polyolefin with polyethylene and ethylene vinyl acetate being preferred. The catheter shaft is not intended to be limited to the dual-lumen embodiment of FIG. 3. Rather, catheters having coaxial lumens as well as catheters having three or more lumens can be used as the delivery catheter. Additionally, single lumen embodiments, such as balloon-on-wire systems can be used with the present invention.

Figure 4:
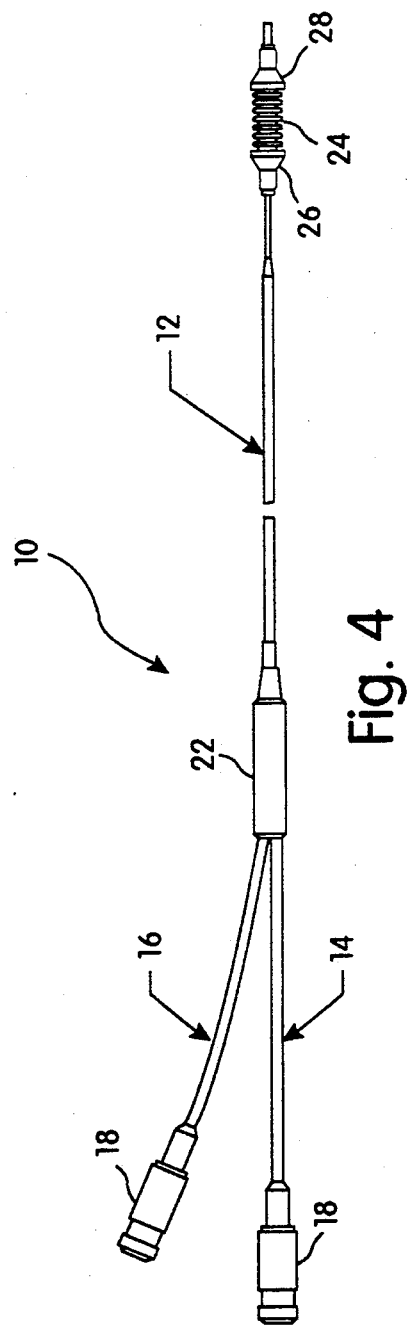
FIG. 4 is an illustration of a stent delivery system in accordance with the invention prior to expansion of the stent.
Figure 5:
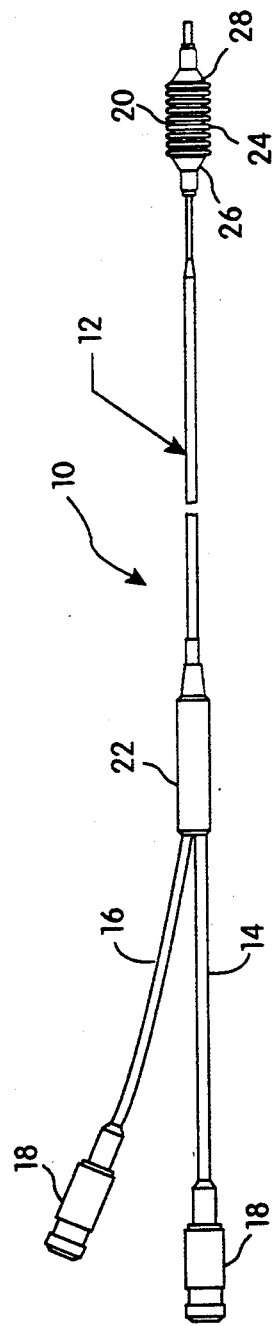
FIG. 5 is an illustration of the stent delivery system with the stent in the expanded configuration.
Figure 6:
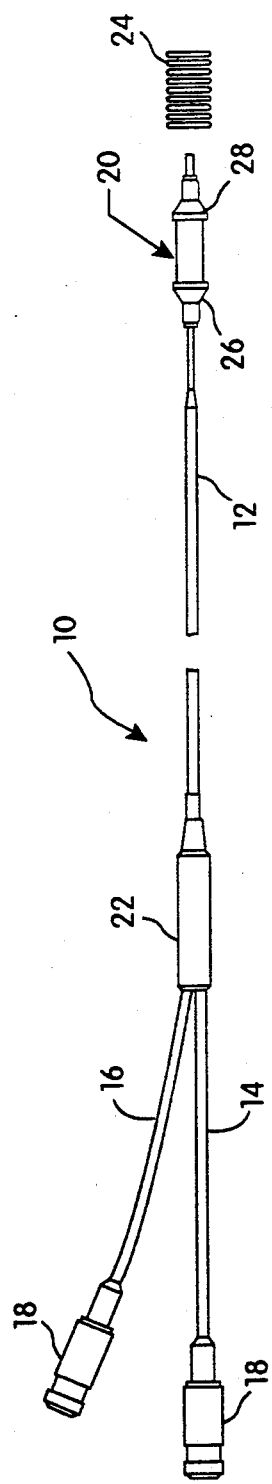
FIG. 6 is an illustration of the stent delivery system upon withdrawal of the introducer.

The operation of the stent delivery system is shown generally in FIGS. 4-6. In FIG. 4, the system comprises a dilatation catheter, generally represented as 10, comprising a multi lumen catheter shaft 12, having a balloon 20 (concealed), mounted at the distal end of the shaft. The balloon can be fabricated from a variety of polymeric materials, (i.e. vinyl, various polyolefins, PET, nylon), with polyolefins being preferred. The catheter shaft has a pair of lumens including an inflation lumen that communicates with the balloon and a guidewire lumen. The lumens are connected to individual flexible tubular legs 14, 16 through Y-fitting 22. The proximal end of each leg can terminate in a standard luer fitting 18. In this example, leg 14 is in communication with the inflation lumen in the catheter shaft which serves to enable inflation and deflation of the balloon 20, and leg 16 communicates with the guidewire lumen which exits the catheter shaft at its distal tip. A stent 24 in its collapsed state surrounds the balloon and is retained in position by end caps 26, 28 which receive and capture the proximal and distal ends of the stent. The end caps serve to prevent axial displacement of the stent as the delivery system and stent are guided through a patient. The end caps can be formed of any of a variety of resilient polymers including polyurethane, polyester elastomers, styrene-ethylene-butadiene-styrene (SEBS) block copolymers, latexes and silicones. End caps formed of a polyether block amide (marketed by ATOCHEM, INC. under the trademark PEBAX), have been found to be particularly useful. Additionally, the end caps may be coated on the inner or outer diameters' or both with a lubricious material such as a silicone. Such a coating would respectively facilitate stent release or tracability.

As can be seen in FIG. 5, upon inflation of the balloon 20, the stent 24 is radially expanded. Inflation of the balloon 20 also causes end caps 26, 28 to be urged radially and axially away, in umbrella-like fashion from the center of the balloon, so that they retract and release the stent 24. During this motion, the portions of the end caps covering the stent are expanded radially to assist in release of the stent. Subsequently, as shown in FIG. 6, the balloon 20 is deflated and the end caps 26, 28 return to their initial non retracted position. The stent 24 remains in its expanded state, having an interior diameter which approximates the outer diameter of the inflated balloon 20. Once the balloon 20 and end caps 26, 28 have returned to their initial, non-retracted configuration, they have a cross-sectional diameter which is less than that of the interior diameter of the expanded stent. The delivery catheter can then be withdrawn from the patient without affecting the position of the stent. Such a withdrawal allows the delivery catheter to be completely removed from the patient while leaving the expanded stent at a desired location within the patient.

Figure 7A:
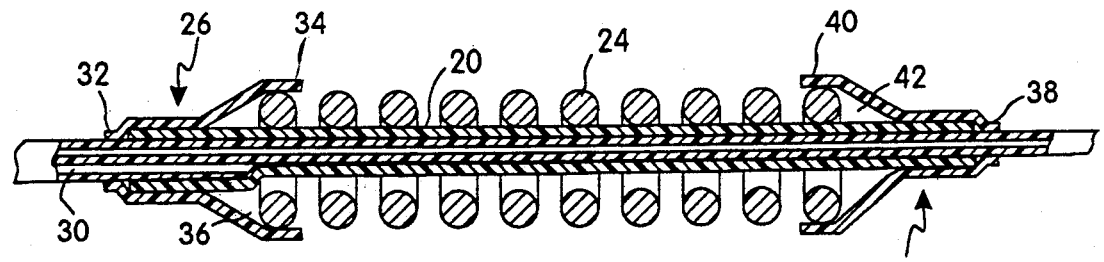
FIGS. 7A-7C are illustrations of the stent delivery system showing the operation of the stent and end caps.
Figure 7B:
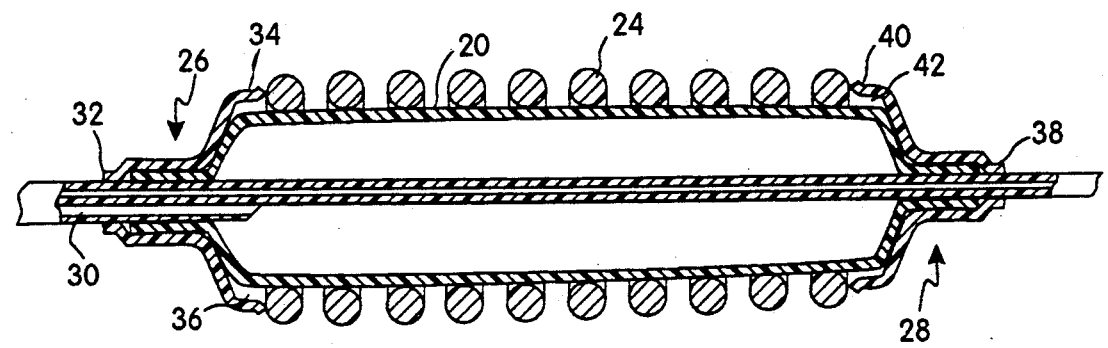
Figure 7C:
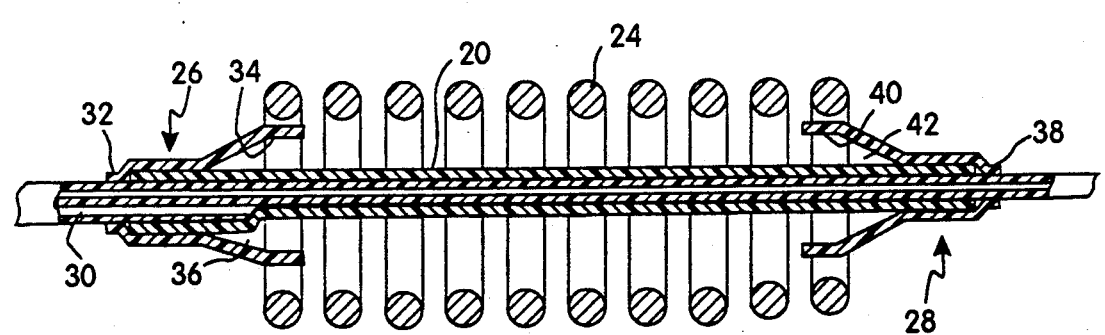

The operation of the end caps is more clearly shown in FIGS. 7A-7C. FIG. 7A shows the stent delivery system and a mounted stent prior to placement of the stent at the stenosis. The balloon 20 is deflated via inflation lumen 30. End cap 26 has a mounting sleeve 32 attached to the catheter shaft at a region adjacent the proximal end of balloon 20. The mounting sleeve can be attached to the catheter shaft using any of a variety of bonding methods. These include, but are not limited to, adhesive bonding, heat bonding and ultrasonic bonding. The bond must provide adequate strength to prevent the mounting sleeve 32 from detaching from the catheter shaft when compression forces are applied to the end cap. An annular socket 34 defined by the end cap surrounds the balloon 20 without contacting it. An annular space 36, defined by the area between the balloon and the annular socket 34 of end cap 26, serves to capture and retain the proximal end of the stent 24.

Similarly, end cap 28 has a mounting sleeve 38 attached to the shaft at a region adjacent the distal end of balloon 20. As with end cap 26, mounting sleeve 38 is attached to the catheter shaft using adhesives, heat, ultrasonic bonding or any of a variety of methods known in the art. An annular socket 40 defined by the end cap surrounds balloon 20 without contacting it. An annular space 42, defined by the area between the balloon and the annular socket 40, serves to capture and retain the distal end of the stent 24. As can be seen in FIG. 7A, the end caps 26, 28 surround the ends of the stent and serve to prevent axial movement of the stent toward either the proximal end or distal end of the delivery catheter. Thus, the catheter can be inserted into a patient without displacing the stent from its position about the balloon.

Once the stent has been placed in a stenosis or dilated stenosis, the balloon is inflated as shown in FIG. 7B. The radial expansion of the balloon 20 imparts a corresponding radial expansion to the stent 24 while simultaneously urging the annular sockets 34, 40 of the end caps 26, 28 away from the stent and toward mounting sleeves 32, 38 of the end caps. In so doing, the end caps 26, 28 retractably release the stent 24.

Finally, as shown in FIG. 7C the balloon is deflated, and the balloon and end caps return resiliently to the configuration shown in FIG. 7A. The stent remains in its expanded position, having an interior diameter corresponding substantially to the outer diameter of the balloon when inflated. The interior diameter of the expanded stent, however, is greater than the outer diameter of the end caps or balloon when the balloon is deflated, and this configuration allows the delivery catheter to be withdrawn from the stent without causing the stent to be moved from its expanded position. Thus, the delivery catheter can be completely withdrawn from the patient while leaving the expanded stent in place.

Figure 8B:
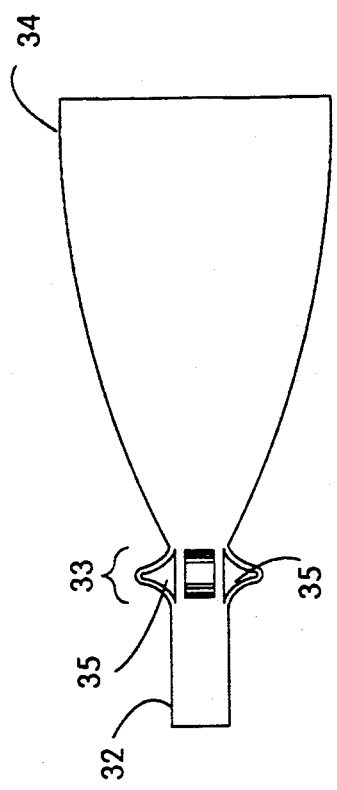
FIGS. 8A and 8B are illustrations of one embodiment of an end cap having a weakened region provided with slits.

In one embodiment, the end caps 26, 28 contain a weakening means for assisting retraction and release of the stent. In one embodiment this weakening means comprises at least one axial slit in a center region of the end cap located between the mounting sleeve and the annular socket which surrounds the balloon. In a preferred embodiment, shown in FIGS. 8A–8B, four axial slits are evenly spaced about the end cap between the mounting sleeve and the annular socket with a spacing of approximately 90° between each. These slits allow the center region of the end caps to collapse axially and bulge outwardly when the annular sockets are urged toward their respective mounting sleeves by the inflated balloon.

Figure 8A:
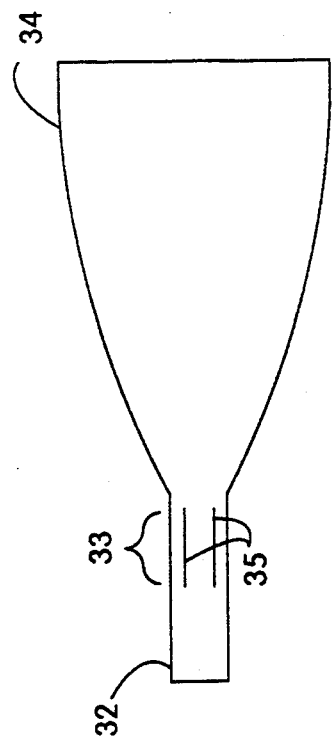

More particularly, FIG. 8A shows an end cap 26 having a mounting sleeve 32 and an annular socket 34. Between the mounting sleeve and the socket is a weakened area 33 having four equidistant slits 35, (of which only two are shown in the figure). Upon application of a radial force to the annular socket 34, such as will occur upon inflation of the balloon, the socket is pushed toward the mounting sleeve 32, causing the weakened area 33 to bulge outwardly from the centerline of the end cap. The retraction of the end cap caused by the radial force causes the annular socket to release the stent. This effect can be seen in FIG. 8B. The weakened area 33 enhances the ease with which the annular socket 34 can be pushed toward the mounting sleeve and therefore eases release of the stent from the socket.

Figure 9B:
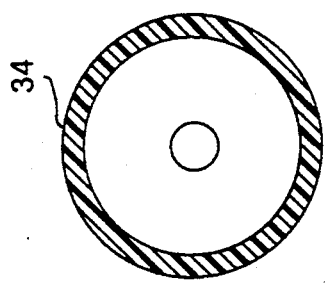
FIGS. 9A and 9B are illustrations of an embodiment of an end cap having a weakened region containing a bulge.
Figure 9A:
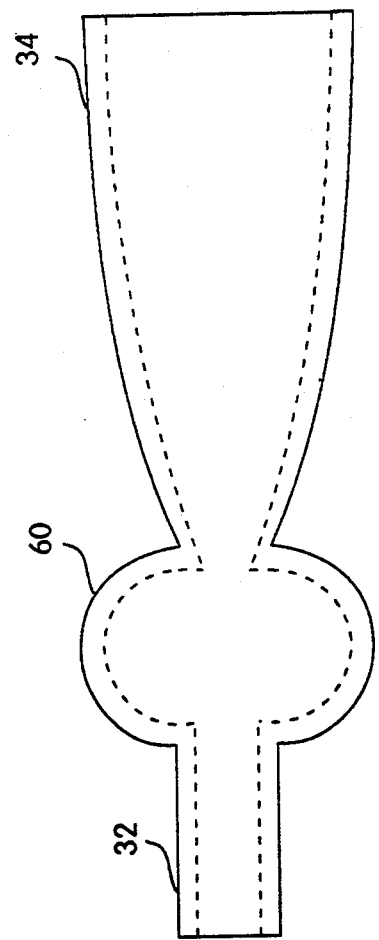

In another embodiment, the weakened region of the end cap located between the mounting sleeve and the annular socket which surrounds the balloon is formed to have a larger interior diameter than the mounting sleeve. In a preferred embodiment, this larger interior diameter is provided as a preformed bulge which allows the annular socket of the cap surrounding the balloon to be pushed toward the mounting sleeve when the balloon is inflated. As before, the retraction of the end cap caused by the radial force causes the annular socket to release the stent. An end cap of this design is shown in FIGS. 9A–9B. FIG. 9A is a cross-sectional elevation of the basic end cap. As can be seen in FIG. 9A, a bulge 60, is located between the mounting sleeve 32 of the end cap and the annular socket 34 of the end cap. The mounting sleeve is affixed to the catheter shaft at a region adjacent to the balloon and the annular socket 34 surrounds the balloon and, prior to expansion, the stent 24. The bulge 60 provides a region of lessened resistance to axial contraction of the end cap and thereby facilitates release of the stent 24 by the annular socket 34 of the end cap when the balloon is inflated. FIG. 9B is an end view of the end cap of FIG. 9A. As can be seen in FIG. 9B, the interior diameter of the annular socket 34 of the end cap is symmetrical, decreasing radially toward the proximal end of the end cap.

Figure 10B:
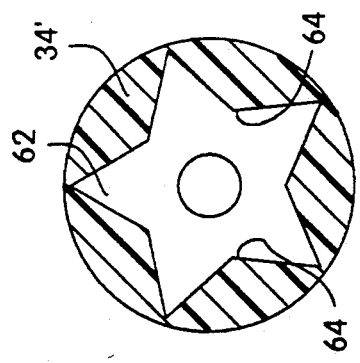
FIGS. 10A and 10B are illustrations of a second embodiment of an end cap having a weakened region containing a bulge.
Figure 10A:
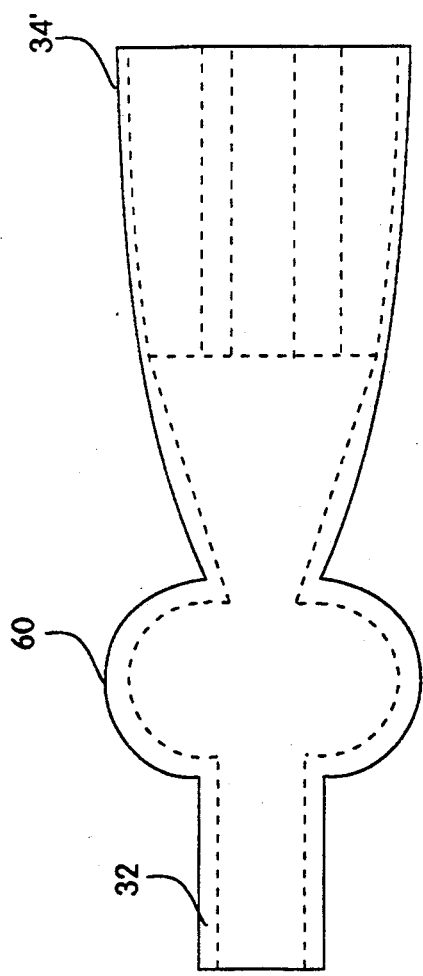

In another embodiment of the end cap, shown in FIGS. 10A–10B, the interior diameter of the annular socket 34' of the end cap is asymmetrical. Such a configuration is intended to minimize contact of the interior surface of the annular socket 34' of the end cap with the stent 24, thereby lowering friction between the annular socket 34' of the end cap and the stent 24. This configuration increases the ease of release of the stent by lowering frictional resistance to retraction of the annular socket 34' of the end cap. As in the embodiment of the end cap shown in FIGS. 9A and 9B, the mounting sleeve of the end cap and the bulge 60 are unchanged. FIG. 10B shows one embodiment of an end cap having an asymmetrical inner diameter of its annular socket 34'. In FIG. 10B the interior diameter 62 of the annular socket 34' is "star-shaped". Thus, the only contact with the stent is along five raised ridges 64 which contact the stent about its circumference. By contacting the stent 24 only along five lines, the end cap can slidably release the stent with ease.

Figure 11B:
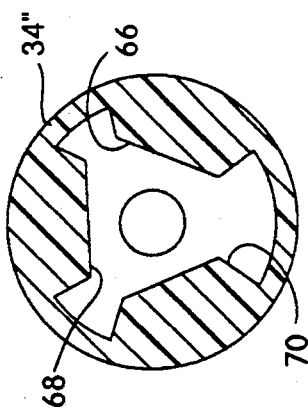
FIGS. 11A and 11B are illustrations of a third embodiment of an end cap having a weakened region containing a bulge.
Figure 11A:
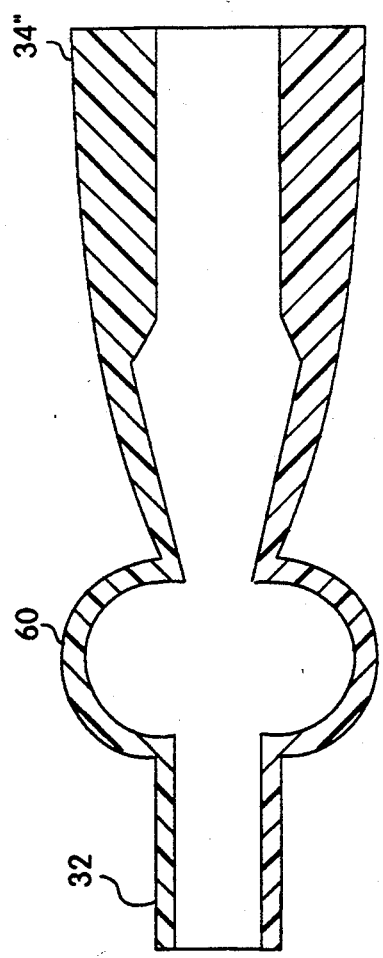

Another embodiment of the end cap is shown in FIGS. 11A–11B. In this embodiment, the annular socket 34" of the end cap again has an asymmetrical interior diameter. However, this asymmetrical interior diameter is formed by three ridges 66, 68, 70 contained within the end cap. These ridges serve to minimize contact of the interior of the annular socket 34" of the end cap and thereby enhance the retraction of the annular socket 34" of the end cap from the stent. As before, bulge 60 and mounting sleeve 32 remain unchanged.

Still another embodiment of the stent introducer system of the present invention is shown in FIG. 12. In FIG. 12, the system is similar to that depicted in FIG. 1 and comprises a modified dilatation catheter generally represented as 80, comprising a multi-lumen catheter shaft 12, having a balloon 20 (not visible), positioned at its distal end. The lumens of the catheter shaft are connected to individual flexible tubular legs 14, 16 through Y-fitting 22. The proximal end of each leg can terminate in a standard luer fitting 18. In this example, leg 14 is in communication with the inflation lumen in the catheter shaft which serves to enable inflation and deflation of the balloon 20, and leg 16 communicates with the quidewire lumen which exits the catheter shaft at its distal tip. A stent 24 in its collapsed state surrounds the balloon and is retained in position by end caps 26 and 28'. The operation of end cap 26 is the same as described previously. End cap 28', however, does not have an annular socket surrounding the stent. Rather, end cap 28' is affixed to the catheter and surrounds the distal portion of the balloon 20. This end cap 28' is formed of a resilient thermoplastic elastomer such as KRATON (trademark of Shell for SEBS block copolymers) and preferably exhibits a higher coefficient of friction than the material of end cap 26, although end caps 26 and 28' could be formed of the same material. Stent 24 surrounding the balloon also surrounds the proximal end of end cap 28'. Contacting the stent and the proximal portion of end cap 28' results in a frictional force which prevents the stent 24 from sliding off the distal end of the delivery catheter 80 if the delivery catheter is moved in the proximal direction. The distal end of delivery catheter 80 is more clearly shown in FIGS. 13A–13C.

Figure 13A:
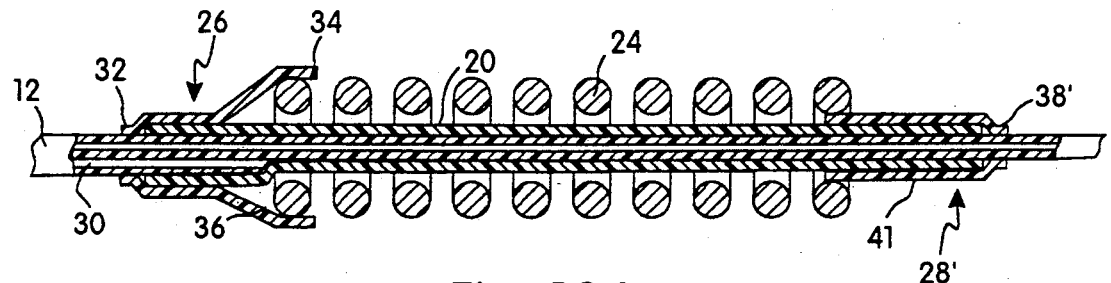
FIGS. 13A-13C are illustrations of the second embodiment of the stent delivery system showing the operation of the stent and the end caps.

FIG. 13A shows the distal end of the stent delivery system of FIG. 12 prior to placement of the stent. The balloon 20 is deflated via inflation lumen 30. End cap 26 has a mounting sleeve 32 attached to the catheter shaft at a region adjacent to the proximal end of balloon 20. Attachment of end cap 26 to the catheter shaft is as described previously. An annular socket 34 defined by the end cap surrounds the balloon 20 without contacting it. An annular space 36 is defined by the area between the balloon and the annular socket 34 of end cap 26. End cap 28' has a mounting sleeve 38' attached to the shaft at a region adjacent the distal end of balloon 20. Mounting sleeve 38' is attached to the catheter shaft using the same methods described previously. An annular friction zone 41 defined by end cap 28' surrounds balloon 20 and is in contact with the balloon. Unlike the proximal end cap 26, there is no annular space between the annular friction zone 41 of end cap 28' and balloon 20. In FIG. 13A, the delivery catheter is shown with a stent 24 in position surrounding the balloon. The proximal end of stent 24 is positioned in annular space 36 and the distal end of stent 24 surrounds the annular friction zone 41 of end cap 28'. As can be seen in FIG. 13A, the end cap 26 surrounds the proximal end of the stent 24 and serves to prevent axial movement of the stent toward the proximal end of the delivery catheter. Axial movement of the stent toward the distal tip of the delivery catheter is prevented by a frictional force between the interior diameter of the distal end of the stent and the outer surface of the annular friction zone 41 of end cap 28'. Thus, at the distal end of the stent delivery system 80, the stent is not locked in place by an annular socket, but rather, is retained by friction. As before, the delivery catheter can be inserted into a patient without displacing the stent from its position surrounding the balloon and the annular friction zone 41 of the distal end cap 28'.

Figure 13B:
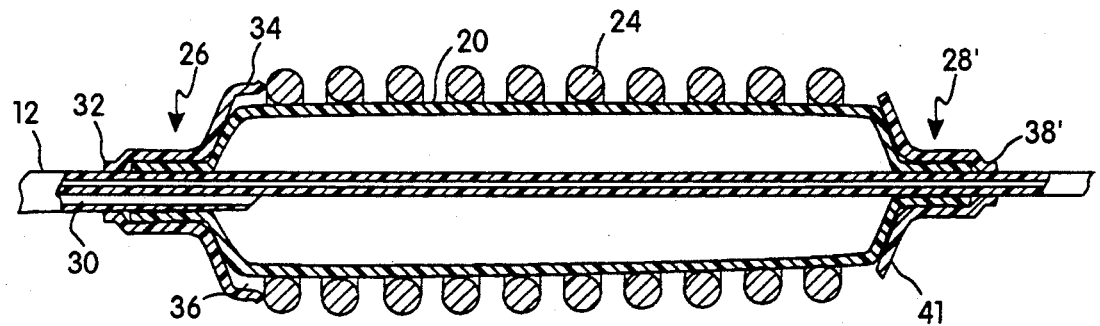

Once the stent has been placed in a stenosis or dilated stenosis, the balloon is inflated as shown in FIG. 13B. The radial expansion of the balloon 20 imparts a corresponding radial expansion to the stent 24 while simultaneously urging the annular socket 34 of end cap 26 away from the stent and toward the mounting sleeve 32 of end cap 28. In so doing, end cap 26 retractably releases the proximal end of the stent. The distal end of the stent 24 surrounding annular friction zone 41 of end cap 28' is expanded, with the balloon, away from the annular friction zone 41 of the end cap 28'. Thus, at the distal end of the stent delivery system 80, inflation of balloon 20 causes the stent 24 to release end cap 28'. During this inflation, the annular friction zone 41 of end cap 28' continues to surround and compress the distal end of balloon 20 thereby helping to maintain a uniform inflation pressure within the balloon.

Figure 13C:
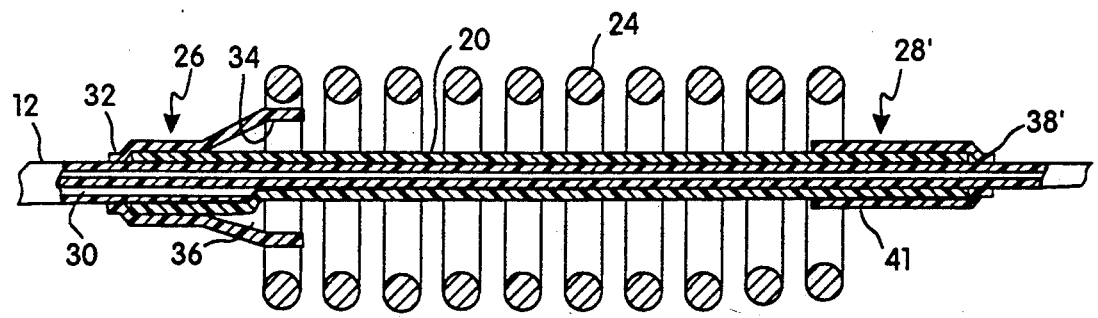

Finally, as shown in FIG. 13C, the balloon is deflated, and the balloon and end caps 26 and 28' return resiliently to the configuration shown in FIG. 13A. The stent remains in its expanded position, having an interior diameter corresponding substantially to the outer diameter of the balloon when the balloon was inflated. The interior diameter of the stent, however, is greater than the outer diameter of end caps 26 and 28', and that of the balloon when the balloon is deflated. This configuration allows the catheter to be withdrawn from the stent without causing the stent to be moved from its expanded position. Thus, the catheter can be completely withdrawn from the patient while leaving the expanded stent in place. This embodiment differs from the embodiment shown in FIGS. 7A-7C since, rather than retaining the distal end of the stent by surrounding it within a socket, retention of the distal end of the stent is accomplished by friction. Although not as secure as an end cap configuration which surrounds the stent, the annular friction zone 41 of end cap 28' is secure enough to maintain the stent in position during the far less frequent movement of the delivery catheter in the proximal direction. The use of an end cap having an annular friction zone also provides a simple and effective stent release mode.

Figure 14:
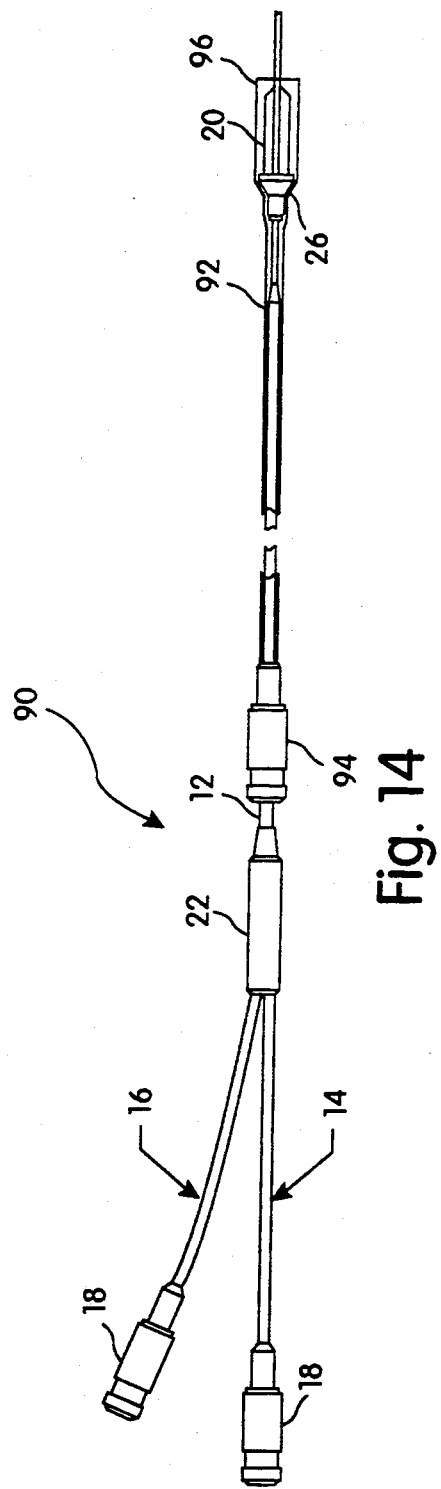
FIG. 14 is an illustration of a third embodiment of the stent delivery system employing a proximal end cap and a retractable sheath.

Another embodiment of the stent introducer is shown in FIG. 14. In this embodiment, the delivery catheter is provided with a stiff retractable sheath which surrounds the stent prior to expansion. More specifically, the delivery catheter, generally represented as 90, comprises a multi-lumen catheter shaft 12, having a balloon 20 positioned at its distal end. The lumens of the catheter shaft are connected to individual flexible tubular legs 14, 16 through Y-fitting 22. The proximal end of each leg can terminate in standard luer fitting 18. In this example, leg 14 is in communication with the inflation lumen in the catheter shaft which serves to enable inflation and deflation of the balloon 20, and leg 16 communicates with the guidewire lumen which exits the catheter shaft at its distal tip. A stent in its collapsed state surrounds the balloon and is captured and retained at its proximal end by end cap 26. End cap 26 and its relationship to the proximal end of the stent is as described in the previous embodiments.

As further shown in FIG. 14, a stiff, elongate, tubular sheath 92 surrounds the stent and a section of the catheter located proximally to end cap 26. The sheath is preferably of a strong yet thin construction and ideally should have a lubricious surface. A stiff, polymeric film such as polyethylene is generally preferred as the sheath material.

The proximal end of the sheath is connected to a slidable hub 94 which surrounds the catheter shaft in a region located distally to the Y-fitting 22. The distal end 96 of the sheath has a diameter large enough to surround end cap 26 and the stent prior to stent expansion and preferably has a rounded edge to minimize the likelihood of tissue damage as the delivery catheter is advanced through a blood vessel.

In use, the distal end of the delivery catheter is guided to a desired location as described previously. The physician then slides the hub 94 toward the Y-fitting. In so doing, the distal end of the sheath is withdrawn from the distal end of the introducer, thereby exposing the stent. The balloon is then inflated to expand the stent as described previously. Subsequently, the balloon is deflated and the delivery catheter is withdrawn, thereby leaving the expanded stent in the predetermined location.

The sheath protects the interior walls of the blood vessels from abrasion caused by the stent as the delivery catheter is advanced through the vessel and also prevents the stent from inadvertently slipping off the distal end of the delivery catheter when the delivery catheter is moved proximally. The sheath provides a lubricious surface between the stent and the wall of the blood vessel through which the delivery catheter travels. The lubricious surface acts as a barrier between the wall and the stent to thereby protect the blood vessel from damage caused by contact with the moving stent and also prevents frictional forces between the wall and the stent from pulling the stent off the distal tip of the delivery catheter. Additionally, since the sheath is provided with a lubricious surface, friction is reduced at the distal tip of the delivery catheter, thereby providing the added advantage of ease of movement of the delivery catheter.

The above embodiment can be combined with either of the two designs described previously. For example, a retractable sheath can be used in combination with the dual socket introducer design depicted in FIGS. 4-7, or it can be used in combination with the annular friction zone design depicted in FIGS. 12 and 13. Thus, in the former example, a delivery catheter having two end caps, each having an annular socket surrounding one end of the stent, can be provided with a retractable sheath which surrounds the unexpanded stent during delivery to the stenosis. Once the stent has been guided to the stenosis, the sheath can be retracted and the stent can be expanded via inflation of the balloon. The end caps will release the stent as previously described. The balloon can then be deflated and the delivery catheter can be withdrawn. In the latter example, a delivery catheter having a proximal end cap with a socket and a distal end cap with an annular friction zone can be provided with a retractable sheath which surrounds the unexpanded stent during delivery to the stenosis. Once the stent has been guided to the stenosis, the sheath can be retracted and the stent can be expanded via inflation of the balloon. The end caps will release the balloon as previously described. The balloon can then be deflated and the delivery catheter can be withdrawn. In each of these embodiments, the retractable sheath provides the stent delivery system with a lubricious shield at its distal end which further reduces the risk of inadvertant stent movement during delivery of the stent to the stenosis.

Figure 15:
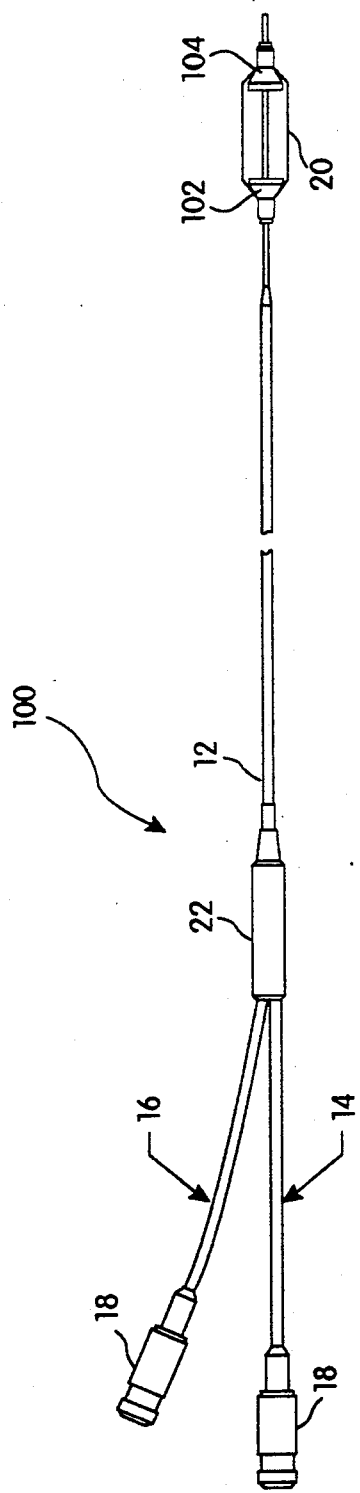
FIG. 15 is an illustration of a fourth embodiment of the stent delivery system showing a delivery catheter having two interior end caps mounted within an inflated balloon.
Figure 16:
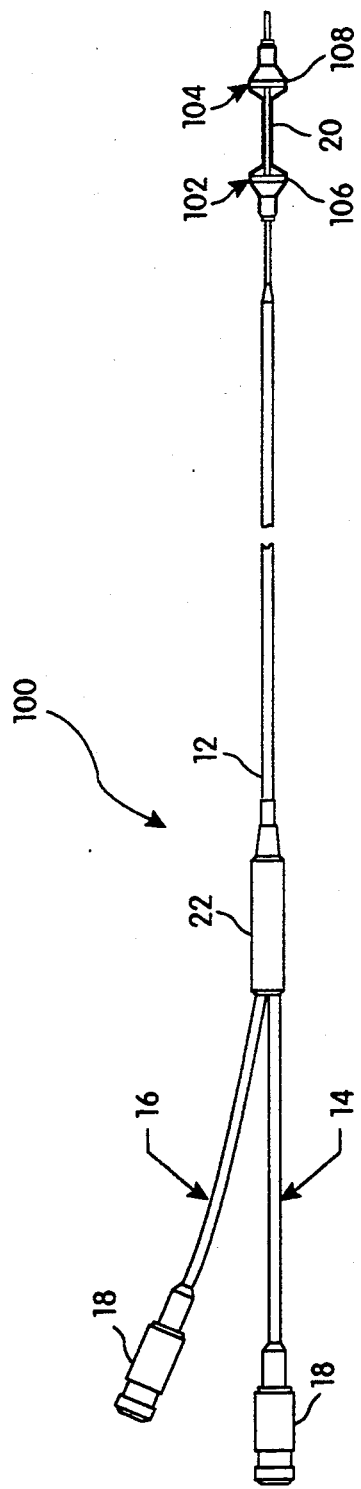
FIG. 16 is an illustration of the fourth embodiment of the stent delivery system showing a delivery catheter having a deflated balloon prior to stent loading.
Figure 17:
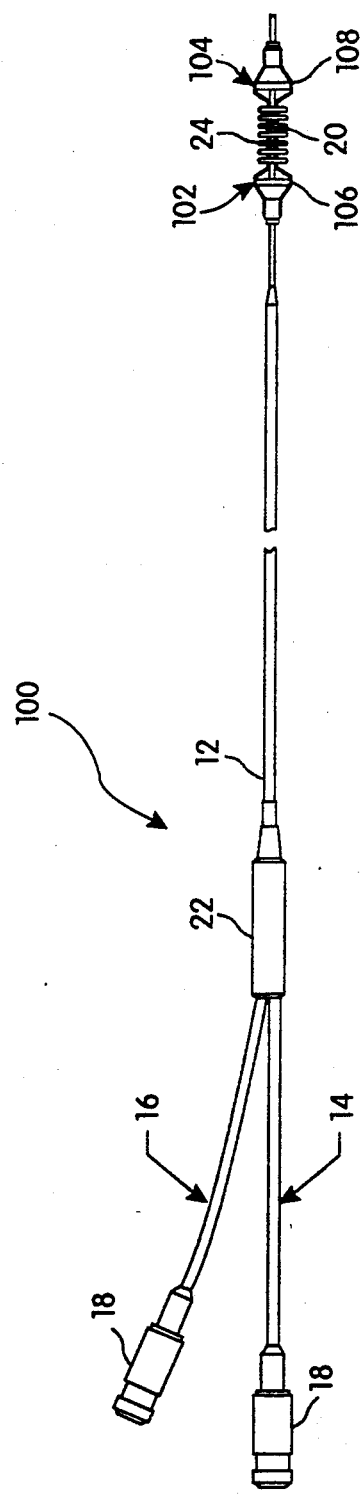
FIG. 17 is an illustration of the fourth embodiment of the stent delivery system showing a stent loaded onto the delivery catheter.

In still another embodiment, depicted in FIGS. 15-17, the delivery catheter can have retention means placed under the balloon rather than over the balloon. FIG. 15 shows such a delivery catheter 100 having two end caps 102, 104 located inside of the balloon 20. As before, the delivery catheter 100 comprises a multi-lumen catheter shaft 12, having a balloon 20, positioned at its distal end. The lumens of the catheter shaft are connected to individual tubular legs 14, 16 through Y-fitting 22. In this example, leg 14 is in communication with the inflation lumen in the catheter shaft which serves to enable inflation and deflation of the balloon 20, and leg 16 communicates with the guidewire lumen which exits the catheter shaft at its distal tip. End caps 102, 104 are located beneath the balloon at respectively, the proximal and distal ends of the balloon.

The ends caps are formed of a flexible, polymeric material, preferably polyethylene or an ionomer, and are each mounted at one end to the catheter shaft which passes through the interior of the balloon. In one embodiment, the end caps have a generally conical form and a wall thickness of at least about 3 mil. Each end cap has at least one slit, extending from its wider end toward its narrower end and being approximately 2.0 to 2.5 mm in length. The slit allows the end cap to collapse around the catheter shaft when the balloon is deflated and the stent is placed on the catheter.

Alternatively, the end cap can be formed from a segment of tubing having uniform diameter. In such an embodiment, the tubing is again provided with at least one slit which starts at one end and travels in an axial direction for approximately 2.0 to 2.5 mm. Subsequent to being slit, the slit end of the end cap is flared on a hot mandril to form a wider, yet compressible end.

FIG. 16 depicts the delivery catheter 100 with balloon 20 deflated prior to loading the stent. Two shoulders 106, 108, formed respectively by end caps 102, 104 are formed on the exterior surface of the balloon by the resilient forces of the end caps on the balloon interior. When a stent is loaded onto the distal end of the delivery catheter, at least the distal end cap is caused to collapse toward the catheter shaft, thereby allowing the stent to pass over it. Once the stent is positioned between the two end caps, they return to their original position as shown in FIG. 16, thereby forming shoulders 106, 108.

A delivery catheter having a stent loaded thereon is shown in FIG. 17. In the Figure, the stent 24 surrounds a portion of the exterior surface of balloon 20. The end caps 102, 104 form shoulders 106, 108 which extend above the ends of the stent, and thereby hold the stent in place as the delivery catheter is guided to a selected location. Once at that location, the balloon is inflated, expanding the stent and causing the stent to have an interior diameter larger than the exterior diameter of the end caps. Subsequently, the balloon is deflated and the delivery catheter is withdrawn, leaving the stent in place.

Various combinations of interior and exterior end caps can be used as well. For example, a delivery catheter having one end cap as shown in FIG. 7A and one end cap as shown in FIG. 15 can be used. In one non-limiting embodiment, such a delivery catheter can have an exterior end cap mounted at the proximal end of the balloon and an interior end cap mounted at the distal end of the balloon.

As a further variation, at least one inner end cap can be fabricated from a shape memory polymer. In such an embodiment, the end cap can be designed to remain collapsed against the catheter when maintained at room temperature. However, when heated to body temperature upon insertion into a patient, the end cap will expand at one end to form a shoulder on the balloon surface. Such a design provides ease of stent loading in combination with stent retention when the delivery catheter is used.

From the foregoing, it will be appreciated that the invention provides an improved system for delivering a stent to a stenosis site. The invention enables a stent to be securely retained by a delivery catheter until it is navigated to a desired location. Subsequently, the stent is expanded and released by the delivery catheter, and the delivery catheter is withdrawn, leaving the expanded stent in place.

It should be understood, however, that the foregoing description of the invention is intended merely to be illustrative thereof and that other modifications, embodiments and equivalents may be apparent to those skilled in the art without departing from the spirit.

Having thus described the invention, what I desire to claim and secure by Letters Patent is:

1. A stent introducer systems comprising: a catheter comprising a flexible elongate catheter shaft having an inflatable balloon located adjacent the distal end thereof;
   the inflatable balloon having a first, unexpanded exterior diameter and a second, expanded exterior diameter;
   at least one flexible end cap having a mounting sleeve affixed to the catheter shaft at a region adjacent one end of the balloon and an annular socket surrounding a portion of the balloon, the annular socket having an interior diameter that is greater than the first, unexpanded exterior diameter of the balloon to create an annular zone between the socket and the unexpanded balloon; and
   an expandable stent surrounding at least a portion of the balloon, wherein at least a portion of the stent is contained within the annular zone;
   the apparatus being such that, upon expansion of the balloon, the stent is released from the annular zone.

2. A stent introducer system as in claim 1 having two flexible end caps, each end cap having a mounting sleeve affixed to the catheter shaft at a region adjacent one end of the balloon and an annular socket surrounding a portion of the balloon, the annular socket having an interior diameter that is greater than the first unexpanded exterior diameter of the balloon to create an annular zone between the socket and the unexpanded balloon.

3. A stent introducer system as in claim 1 having a first end cap affixed to the catheter shaft adjacent the proximal portion of the balloon.

4. A stent introducer system as in claim 3 having a distal end cap having a mounting sleeve affixed to the catheter adjacent to the distal portion of the balloon and an annular friction zone surrounding the distal portion of the balloon and surrounded by a distal portion of the stent, the apparatus being such that, upon expansion of the balloon, the stent is released from the annular zone of the proximal end cap and the distal end cap is released from the stent.

5. A stent introducer system as in claim 1 wherein the end cap includes a weakening means for assisting release of the stent.

6. A stent introducer system as in claim 5 wherein the weakening means comprises at least one axial slit in the end cap, the slit being located in a region between the mounting sleeve and the annular socket.

7. A stent introducer system as in claim 6 wherein the weakening means comprises four axial slits spaced evenly about the end cap.

8. A stent introducer system as in claim 5 wherein the weakening means comprises a region of increased inner diameter of the end cap, the region being located between the mounting sleeve and the annular socket.

9. A stent introducer system as in claim 1 wherein the end cap comprises a flexible elastomer.

10. A stent introducer system as in claim 1 which additionally comprises a sheath means surrounding the stent and a section of the catheter shaft located proximally thereto; said sheath means being slideable in the proximal direction to expose the stent prior to expansion thereof.

11. A stent introducer system as in claim 10 wherein the sheath means comprises a polymeric cylinder.

12. A stent introducer system as in claim 11 wherein the sheath means comprises a polyethylene.

13. A stent introducer system as in claim 10 wherein the sheath means has a lubricious surface.

14. A stent introducer system comprising:
a catheter comprising a flexible elongate catheter shaft having an inflatable balloon located adjacent the distal end thereof; and
at least one flexible end cap having a mounting sleeve affixed to the catheter shaft at a region adjacent one end of the balloon and an annular socket surrounding said one end of the balloon to thereby define an annular space between the balloon and the socket.

15. A stent introducer system as in claim 14 having two flexible end caps, each end cap having a mounting sleeve affixed to the catheter shaft at a region adjacent one end of the balloon and an annular socket surrounding said one end of the balloon to thereby define an annular space between the balloon and the socket.

16. A stent introducer system as in claim 15 wherein each end cap includes a weakening means in the region between the mounting sleeve and the annular socket.

17. A stent introducer system as in claim 16 wherein the weakening means comprises at least one axial slit in the end cap in the region between the mounting sleeve and the annular socket.

18. A stent introducer system as in claim 16 wherein the weakening means comprises a region of increased inner diameter of the end cap, the region being located between the mounting sleeve and the annular socket.

19. A stent introducer system as in claim 14 having a proximal end cap affixed to the catheter shaft at a region adjacent the proximal end of the balloon, said proximal end cap having an annular socket surrounding the proximal end of the balloon to thereby define an annular space between the balloon and the socket; and
a distal end cap having a mounting sleeve affixed to the catheter adjacent to the distal end of the balloon and an annular friction zone for contacting an interior portion of a stent, the distal end cap surrounding the distal portion of the balloon.

20. A stent introducer system as in claim 14 which additionally comprises a sheath means surrounding the stent and a section of the catheter shaft located proximally thereto; said sheath means being slideable in the proximal direction to expose the balloon.

21. A stent introducer system as in claim 20 wherein the sheath means comprises a polymeric cylinder.

22. A stent introducer system as in claim 21 wherein the sheath means comprises a polyethylene.

23. A stent introducer system as in claim 20 wherein the sheath has a lubricious surface.

24. A method for introducing a stent into a patient, the method comprising the steps of:
a) providing a stent introducer comprising:
a catheter comprising a flexible, elongate catheter shaft having an inflatable balloon located adjacent the distal end thereof;
the inflatable balloon having a first, unexpanded exterior diameter and a second, expanded exterior diameter;
at least one flexible end cap having a mounting sleeve affixed to the catheter shaft at a region adjacent one end of the balloon and an annular socket surrounding a portion of the balloon, the annular socket having an interior diameter that is greater than the first, unexpanded exterior diameter of the balloon to create an annular zone between the socket and the unexpanded balloon; and
an expandable stent surrounding at least a portion of the balloon, wherein at least a portion of the stent is contained within the annular zone;
b) inserting the stent introducer into a blood vessel of the patient;
c) guiding the introducer to a selected site;
d) inflating the balloon to thereby expand and seat the stent at the selected site;
e) deflating the balloon; and
f) withdrawing the introducer from the patient.

25. A method for introducing a stent into a patient, the method comprising the steps of:
a) providing a stent introducer comprising:
a catheter comprising a flexible, elongate catheter shaft having an inflatable balloon located adjacent the distal end thereof;
the inflatable balloon having a first, unexpanded exterior diameter and a second, expanded exterior diameter;
at least one flexible end cap having a mounting sleeve affixed to the catheter shaft at a region adjacent one end of the balloon and an annular socket surrounding a portion of the balloon, the annular socket having an interior diameter that is greater than the first, unexpanded exterior diameter of the balloon to create an annular zone between the socket and the unexpanded balloon;
an expandable stent surrounding at least a portion of the balloon, wherein at least a portion of the stent is contained within the annular zone; and,
a sheath means surrounding the stent and a section of the catheter shaft located proximally thereto, said sheath means being slideable in the proximal direction to expose the stent prior to expansion thereof;
b) inserting the stent introducer into a blood vessel of the patient;
c) guiding the catheter to a selected site;
d) sliding the sheath in the proximal direction to expose the stent;
e) inflating the balloon to thereby expand and seat the stent at the selected site;
f) deflating the balloon; and
g) withdrawing the introducer from the patient.

26. A stent introducer system comprising;
a catheter comprising a flexible elongate catheter shaft having an inflatable balloon located adjacent the distal end thereof; and
at least one flexible end cap mounted on the catheter shaft in the interior of the balloon at a region adjacent one end of the balloon.

27. A stent introducer system as in claim 26 having two flexible end caps, each mounted on the catheter shaft in the interior of the balloon, one each of said end caps being located adjacent the proximal and distal ends of the balloon.

28. A stent introducer system as in claim 26 having a first flexible end cap mounted to the catheter shaft in the interior of the balloon at a region adjacent one end of the balloon and a second flexible end cap having a mounting sleeve affixed to the catheter shaft at a region adjacent the other end of the balloon, the second end cap having an annular socket surrounding said other end of the balloon to thereby define an annular space between the balloon and the socket.

29. A stent introducer system as in claim 26 wherein each end cap is wider at one end than at the other end and contains at least one slit extending along a portion of the end cap from the wider end toward the other end.

30. A stent introducer system as in claim 26 wherein at least one end cap is fabricated from a shape memory polymer.

31. A stent introducer system comprising:
a catheter comprising a flexible elongate catheter shaft having an inflatable balloon located adjacent the distal end thereof;
an expandable stent surrounding at least a portion of the balloon; and
at least one flexible end cap mounted on the catheter shaft in the interior of the balloon at a region adjacent one end of the balloon, the end cap defining a shoulder on the exterior surface of the balloon when the balloon is deflated, to maintain the position of the stent on the exterior of the balloon.

32. A stent introducer system as in claim 31 having two flexible end caps, each mounted on the catheter shaft in the interior of the balloon, one each of said end caps being located adjacent the proximal and distal ends of the balloon, said end caps defining a pair of shoulders upon the exterior surface of the balloon when the balloon is deflated, the shoulders defining, in the region between them, the portion of the balloon surrounded by the stent.

33. A stent introducer system as in claim 31 wherein each end cap is wider at one end than at the other end and contains at least one slit extending along a portion of the end cap from the wider end toward the other end.

34. A stent introducer system as in claim 31 wherein at least one end cap is fabricated from a shape memory polymer.

35. A method for introducing a stent into a patient, the method comprising:
a) providing a stent introducer comprising:
a catheter comprising a flexible elongate catheter shaft having an inflatable balloon located adjacent the distal end thereof;
an expandable stent surrounding at least a portion of the balloon; and
at least one flexible end cap mounted on the catheter shaft in the interior of the balloon at a region adjacent one end of the balloon;
b) inserting the stent introducer into a blood vessel of the patient;
c) guiding the introducer to a selected site;
d) inflating the balloon to thereby expand and seat the stent at the selected site;
e) deflating the balloon; and
f) withdrawing the introducer from the patient.

36. A stent introducer system for introducing a stent having a predetermined length into a lumen of a blood vessel comprising:
a catheter having an elongated flexible shaft and an inflatable balloon mounted on the shaft adjacent the distal end of the shaft;
a pair flexible end caps mounted on the catheter shaft, the end caps being disposed adjacent the ends of the balloon and each end cap having at least a portion positioned about a margin of the balloon, the end caps having shoulder-defining surfaces that face each other;
the end caps being spaced so that their shoulder-defining surfaces are spaced from each other a distance no less than the predetermined length of the stent;
whereby the stent may be mounted, in an unexpanded configuration, on the balloon, and between the facing surfaces of the end caps whereby the end caps will define an abutting surface engagable with the ends of the stent, thereby to retain the stent on the balloon.

37. A stent introducer system comprising:
a catheter comprising a flexible, elongate catheter shaft having an inflatable balloon located adjacent to the distal end thereof; and
two flexible end caps, each end cap having a mounting sleeve affixed to the catheter shaft at a region adjacent one end of the balloon and an annular socket surrounding said one end of the balloon to thereby define an annular space between the balloon and the socket, wherein each end cap includes a weakening means in the region between the mounting sleeve and the annular socket.

38. A stent introducer system as in claim 37 wherein the weakening means comprises at least one axial slit in the end cap in the region between the mounting sleeve and the annular socket.

39. A stent introducer system as in claim 37 wherein the weakening means comprises a region of increased inner diameter of the end cap, the region being located between the mounting sleeve and the annular socket.

40. A stent introducer system comprising:
a catheter comprising a flexible, elongate catheter shaft having an inflatable balloon located adjacent to the distal end thereof; and
a first flexible end cap mounted to the catheter shaft in the interior of the balloon at a region adjacent one end of the balloon and second flexible end cap having a mounting sleeve affixed to the catheter shaft at a region adjacent the other end of the balloon, the second end cap having an annular socket surrounding said other end of the balloon to thereby define an annular space between the balloon and the socket.

41. A stent introducer system comprising:
a catheter comprising a flexible elongate catheter shaft having an inflatable balloon located adjacent to the distal end thereof; and
at least one flexible end cap mounted on the catheter shaft in the interior of the balloon in a region adjacent one end of the balloon wherein each of said at least one flexible end cap is wider at one end than at the other end and contains at least one slit extending along a portion of the end cap from the wider end toward the other end.

42. A stent introducer system comprising:
a catheter comprising a flexible, elongate catheter shaft having an inflatable balloon located adjacent the distal end thereof;
an expandable stent surrounding at least a portion of the balloon; and
at least one flexible end cap mounted on the catheter shaft in the interior of the balloon at a region adjacent one end of the balloon, the end cap defining a shoulder on the exterior surface of the balloon when the balloon is deflated, to maintain the position of the stent on the exterior of the balloon, and further wherein each of said at least one flexible end cap is wider at one end than at the other end and contains at least one slit extending along a portion of the end cap from the wider end toward the other end.

43. A stent introducer system comprising:
a catheter comprising a flexible, elongate catheter shaft having an inflatable balloon located adjacent the distal end thereof;
an expandable stent surrounding at least a portion of the balloon;
and at least one flexible end cap fabricated from a shape memory polymer and mounted on the catheter shaft in the interior of the balloon at a region adjacent one end of the balloon, the end cap defining a shoulder on the exterior surface of the balloon when the balloon is deflated to maintain the position of the stent on the exterior of the balloon.

* * * * *